United States Patent
Mickle et al.

(10) Patent No.: US 10,870,654 B2
(45) Date of Patent: *Dec. 22, 2020

(54) PHARMACEUTICALLY ACCEPTABLE SALTS AND POLYMORPHIC FORMS OF HYDROCODONE BENZOIC ACID ENOL ESTER AND PROCESSES FOR MAKING SAME

(71) Applicant: KemPharm, Inc., Celebration, FL (US)

(72) Inventors: Travis Mickle, Kissimmee, FL (US); Sven Guenther, Coralville, IA (US); Christal Mickle, Kissimmee, FL (US); Guochen Chi, Coralville, IA (US); Jaroslaw Kanski, Blacksburg, VA (US); Andrea K. Martin, Fincastle, VA (US); Bindu Bera, Blacksburg, VA (US)

(73) Assignee: KemPharm, Inc., Celebration, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/356,938

(22) Filed: Mar. 18, 2019

(65) Prior Publication Data

US 2019/0284197 A1    Sep. 19, 2019

Related U.S. Application Data

(63) Continuation of application No. 16/352,125, filed on Mar. 13, 2019, now abandoned, which is a continuation of application No. 15/730,885, filed on Oct. 12, 2017, now Pat. No. 10,351,574, which is a continuation of application No. 14/773,628, filed as application No. PCT/US2014/022716 on Mar. 10, 2014, now Pat. No. 9,815,844.

(60) Provisional application No. 61/774,756, filed on Mar. 8, 2013.

(51) Int. Cl.
| | |
|---|---|
| *A01N 43/42* | (2006.01) |
| *A61K 31/44* | (2006.01) |
| *C07D 489/04* | (2006.01) |
| *A61K 31/485* | (2006.01) |
| *C07D 489/02* | (2006.01) |

(52) U.S. Cl.
CPC .......... *C07D 489/04* (2013.01); *A61K 31/485* (2013.01); *C07D 489/02* (2013.01); *C07B 2200/13* (2013.01)

(58) Field of Classification Search
CPC ....................................................... A01N 43/42
USPC ............................................................ 514/282
See application file for complete search history.

(56) References Cited

U.S. PATENT DOCUMENTS

| | | |
|---|---|---|
| 7,625,918 B2 | 12/2009 | Hagen et al. |
| 8,461,137 B2 | 6/2013 | Mickle et al. |
| 8,748,413 B2 | 6/2014 | Mickle et al. |
| 8,828,978 B2 | 9/2014 | Mickle et al. |
| 8,927,716 B2 | 1/2015 | Mickle et al. |
| 9,132,125 B2 | 9/2015 | Mickle et al. |
| 2008/0113025 A1 | 5/2008 | Devane et al. |
| 2011/0002990 A1 | 1/2011 | Mickle et al. |
| 2015/0335759 A1 | 11/2015 | Mickle et al. |
| 2016/0039837 A1 | 2/2016 | Heinrich et al. |

FOREIGN PATENT DOCUMENTS

WO    2014138740    9/2014

OTHER PUBLICATIONS

United States Patent and Trademark Office, "Non-Final Office Action," issued in connection with U.S. Appl. No. 14/773,628, dated Feb. 1, 2017, 6 pages.
United States Patent and Trademark Office, "Notice of Allowability," issued in connection with U.S. Appl. No. 14/773,628, dated Sep. 12, 2017, 9 pages.
United States Patent and Trademark Office, "Requirement for Restriction/Election," issued in connection with U.S. Appl. No. 14/773,628, dated Aug. 1, 2016, 8 pages.
International Searching Authority, "International Search Report," issued in connection with International Patent Application No. PCT/US2014/022716, dated Aug. 18, 2014, 4 pages.
International Searching Authority, "Written Opinion," issued in connection with International Patent Application No. PCT/US2014/022716, dated Aug. 18, 2014, 5 pages.
International Bureau of WIPO, "International Preliminary Report on Patentability," issued in connection with International Patent Application No. PCT/US2014/022716, dated Sep. 8, 2015, 6 pages.
United States Patent and Trademark Office, "Notice of Allowance," issued in connection with U.S. Appl. No. 14/773,628, dated Jul. 13, 2017, 13 pages.

*Primary Examiner* — Layla Soroush
(74) *Attorney, Agent, or Firm* — McAndrews, Held & Malloy, Ltd.

(57) ABSTRACT

Compositions comprising hydrocodone benzoic acid enol ester to form novel prodrugs including hydrocodone benzoic acid enol ester salts, and various polymorphs. Also provided are processes for the preparation of hydrocodone benzoic acid enol ester salts, and various polymorphs.

11 Claims, 14 Drawing Sheets

Hydrocodone benzoic acid enol ester HCl salt crystal forms inter-relation and generic examples

PHARMACEUTICALLY ACCEPTABLE SALTS AND POLYMORPHIC FORMS OF HYDROCODONE BENZOIC ACID ENOL ESTER AND PROCESSES FOR MAKING SAME

The present patent application is a continuation of U.S. patent application Ser. No. 16/352,125, which was filed Mar. 13, 2019, which is a continuation of U.S. patent application Ser. No. 15/730,885, which was filed on Oct. 12, 2017, which is a continuation of U.S. patent application Ser. No. 14/773,628, which was filed on Sep. 8, 2015, which is a 371 of PCT/US2014/022716, filed on Mar. 10, 2014, and is related to and claims the priority benefit of U.S. Provisional Pat. App. Ser. No. 61/774,756, filed Mar. 8, 2013, the content of each of the aforementioned application which is hereby incorporated by reference in its entirety into this disclosure.

FIELD OF THE INVENTION

The present disclosure relates to pharmaceutically acceptable salts and polymorphic forms of hydrocodone benzoic acid enol ester. The disclosure further relates to processes for making the salts and polymorphic forms of hydrocodone benzoic acid enol ester.

BACKGROUND OF THE INVENTION

Hydrocodone benzoic acid enol ester is an opiate prodrug that is useful for overdose prevention. Previous processes for the preparation of hydrocodone benzoic acid enol esters require the isolation of pure hydrocodone from hydrocodone bitartrate before preparation of the benzoic acid enol ester. Such processes are inefficient and expensive. Another drawback to prior art processes is the difficulty in preparing a high quality product. Thus, there remains a need for new processes for making hydrocodone benzoic acid enol esters.

SUMMARY OF THE INVENTION

In one embodiment, the present disclosure provides a substantially pure compound comprising hydrocodone benzoic acid enol ester having a level of impurities less than about 10% to 0.1%. For example, the impurities can be, for example, less than 10% (purity of 90%), less than 5% (purity of 95%), less than 2.0% (purity of 98%), less than 1.0% (purity of 99%/), less than 0.5% (purity of 99.5%), less than 0.1% (purity of 99.9%). In one aspect of this embodiment, the level of impurities is less than 0.1%. In another aspect of this embodiment, the impurities include hydrocodone and benzoic acid.

In another embodiment, the compound may be part of a pharmaceutical composition, such as but not limited to any pharmaceutically acceptable salt of hydrocodone benzoic acid enol ester. According to this aspect, the pharmaceutically acceptable salt may be selected from the group consisting of hydrochloride, hydrobromide, hydrogensulphate, sulphate, maleate, fumarate, oxalate, methanesulfonate, succinate, ascorbate, and tartrate. However, other suitable salts can be used as would be known by one of ordinary skill in the art. Other embodiments of the invention further include polymorphic forms of hydrocodone benzoic acid enol ester hydrochloride such as Forms I, II, III, IV, V, or a combination thereof. In yet another embodiment, a pharmaceutical composition may comprise a polymorphic form of hydrocodone benzoic acid enol ester hydrochloride, such as Form I, II, III, IV, V, or a combination thereof.

In accordance with other embodiments, various polymorphic forms of hydrocodone benzoic acid enol ester hydrochloride are described. The polymorphic form may be one of Form I, II. III, IV, or V, or alternatively may be a combination thereof.

In some embodiments, polymorphic Form I can have an XRPD pattern having XRPD peaks at about the following 2θ values: 6.16, 9.05, 10.95, 11.91, 12.32, 13.16, 14.60, 14.94, 17.04, 17.23, 17.80, 18.57, 19.18, 20.66, 21.10, 22.15, 23.50, 26.07, and 28.39. Polymorphic Form II can have an XRPD pattern having XRPD peaks at about the following 2θ values: 4.31, 8.62, 12.95, 13.19, 13.42, 14.33, 14.97, 15.72, 17.48, 18.47, 21.73, 22.92, 24.15, 24.98, 26.41, 26.53, 26.62, 27.93, and 30.46. Polymorphic Form III can have an XRPD pattern having XRPD peaks at about the following 2θ values: 4.35, 8.68, 13.01, 13.27, 13.86, 14.06, 15.05, 16.02, 18.40, 21.72, 22.38, and 26.14. Polymorphic Form IV can have an XRPD pattern having XRPD peaks at about the following 2θ values: 7.87, 10.27, 11.87, 12.56, 13.18, 14.19, 15.34, 16.77, 17.67, 18.58, 19.50, 20.30, and 21.31. Polymorphic Form V can have an XRPD pattern having XRPD peaks at about the following 2θ values: 6.17, 7.50, 9.04, 10.96, 11.93, 12.34, 12.64, 13.13, 14.34, 14.62, 14.93, 16.73, 17.04, 17.22, 17.81, 18.59, 18.98, 19.19, 19.52, 20.67, 21.10, 21.91, 22.15, 22.82, 23.49, 25.03, 25.37, 26.09, and 26.43.

In another aspect, a solid pharmaceutical composition comprising a therapeutically effective amount of one or more polymorphic forms of hydrocodone benzoic acid enol ester hydrochloride and a pharmaceutically acceptable excipient in a formulation for administration is provided. In one embodiment, the formulation can be designed for oral administration. Accordingly, the solid pharmaceutical composition can be a coated or uncoated tablet, a hard or soft gelatin capsule, a sugar-coated pill, a lozenge, a wafer sheet, a pellet, or a powder. As would be appreciated by one of ordinary skill in the art, however, formulations comprising therapeutically effective amounts of the polymorphic forms disclosed herein may also be designed for other routes of administration. In one aspect of this embodiment, the composition may consist of a pure polymorphic form.

In another aspect, the disclosed subject matter is directed to a process for preparing polymorphic forms of hydrocodone benzoic acid enol ester hydrochloride. In one embodiment, hydrocodone benzoic acid enol ester hydrochloride is prepared by recrystallizing hydrocodone benzoic acid enol ester hydrochloride from an organic solvent in the presence of water. In one embodiment, the process produces polymorphic Form I. For example, polymorphic Form I is formed in instances where the molar ratio of water to hydrocodone benzoic acid enol ester hydrochloride is at least about 0.5, such as about 0.5, 1.0, or more.

In accordance with the process, the organic solvent may be an alcohol, an ether, or ester. For example, the solvent can be selected from ethanol, tert-butyl methyl ether, or ethyl acetate, or a combination thereof.

In another embodiment, the hydrocodone benzoic acid enol ester hydrochloride is recrystallized in an organic solvent containing less than 0.2% water to form polymorphic Form II. The organic solvent may be anhydrous. For example, the solvent may be isopropanol, isopropyl acetate, or a mixture of the two.

In yet another embodiment, polymorphic Form II can be employed to form polymorphic forms III, IV, and V. For example, hydrocodone benzoic acid enol ester hydrochloride Form II can be heated at a temperature of between about 210° C. and about 230° C. to create polymorphic Form III. In another embodiment, hydrocodone benzoic acid enol ester hydrochloride Form II can be exposed to a high relative humidity for a period of time to create Form IV. In one embodiment, the relative humidity is from about 75% to about 100%. Hydrocodone benzoic acid enol ester hydrochloride Form III can be exposed to a high relative humidity for a period of time to create Form V. The relative humidity may be between about 75% and about 100%.

In yet another aspect of the present embodiment, hydrocodone benzoic acid enol ester hydrochloride is prepared in an amorphous form. This form may be prepared by dissolving the hydrocodone benzoic acid enol ester hydrochloride in an organic solvent, then evaporating the solvent.

In another embodiment, a process of preparing hydrocodone benzoic acid enol ester is provided. The process includes heating hydrocodone free base with a benzoylating reagent with or without the presence of a base to form hydrocodone benzoic acid enol ester. The reaction may be heated to between about 80° C. and about 160° C.

In one aspect of this embodiment, the reaction takes place in an organic solvent. Some suitable organic solvents include but are not limited to toluene, dimethylformamide, N-methyl-2-pyrrolidinone, or xylenes. However, other suitable organic solvents can be used as would be known in the art. Alternatively, the reaction proceeds without solvent when using a base capable of at least partially dissolving hydrocodone free base and the benzoylating reagent. The base may be, for example, pyridine, N,N-diisopropylethylamine, diazacycloundecene, triethylamine, or potassium benzoate. Various benzoylating agents may be employed. Some non-limiting examples include benzoic anhydride, benzoyl chloride, benzoyl bromide, N-benzoyloxysuccinimide.

According to another aspect, the hydrocodone benzoic acid enol ester may be converted to its hydrochloric acid salt. According to this embodiment, the hydrocodone benzoic acid enol ester is crystallized from an organic solvent in the presence of approximately 1.1 equivalents of hydrochloric acid.

According to another aspect, a process for making hydrocodone benzoic acid enol ester is provided in which hydrocodone benzoic acid enol ester can be created from hydrocodone and a benzoylating reagent in one step. The possibility to perform this reaction in one step provides an advantage over prior art methods such as U.S. patent application Ser. No. 12/828,381, which discloses a two-step addition process. The present one-step method is also robust enough to use crude hydrocodone as a starting material, which provides an advantage over prior art methods requiring pure hydrocodone as a starting material.

DETAILED DESCRIPTION OF EXEMPLARY EMBODIMENTS

Figure 1:
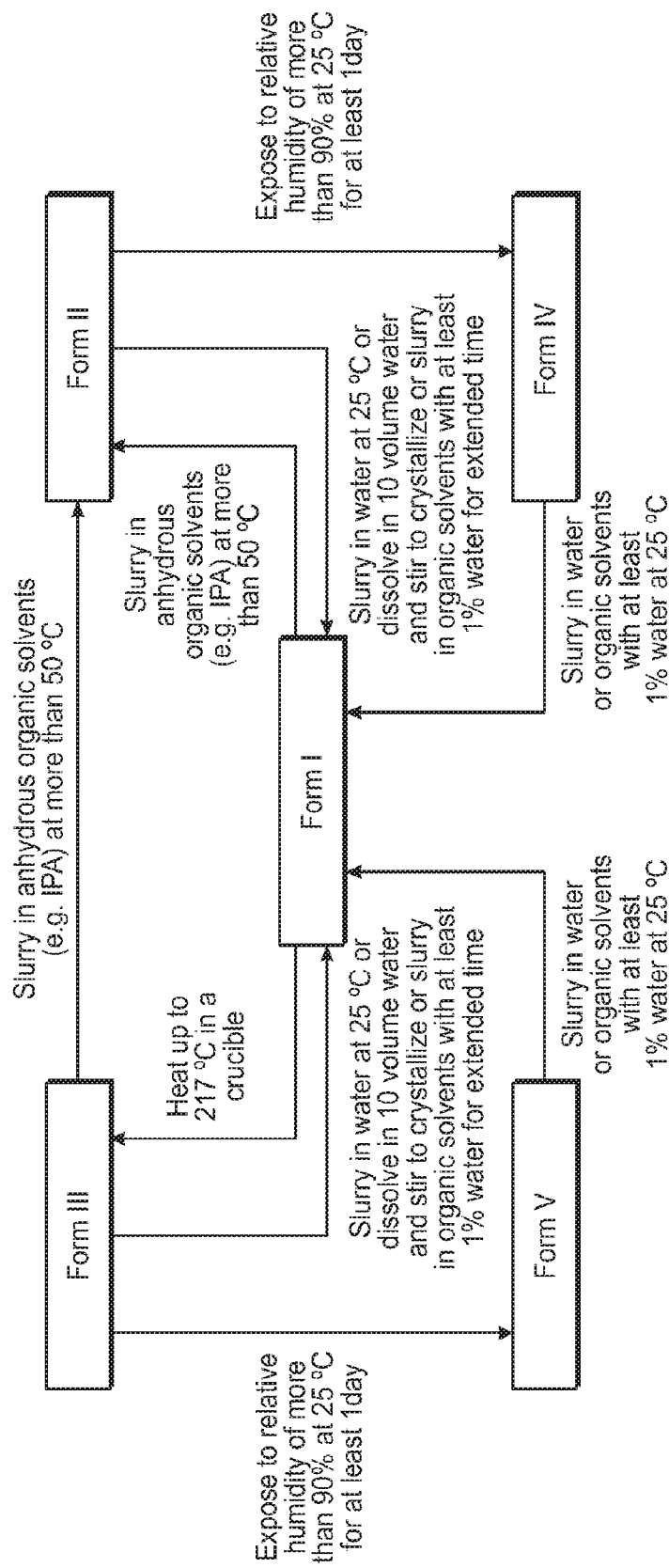
FIG. 1 is a chart depicting the inter-relation of hydrocodone benzoic acid enol ester HCl salt crystal forms.

In a first aspect, the present disclosure provides a pharmaceutically acceptable salt of hydrocodone benzoic acid enol ester, and processes for making the pharmaceutically acceptable hydrocodone benzoic acid enol ester salt. Prior methods for making hydrocodone benzoic acid enol ester required the isolation of pure hydrocodone (through the bitartrate) before preparation of the benzoic acid enol ester. It has been found that this purification step is not required. Advantageously, the process of the present disclosure eliminates the purification step thereby providing a more efficient process of making hydrocodone benzoic acid enol ester, it salts, and various polymorphic forms. Moreover, the presently described process provides a pure hydrocodone benzoic acid enol ester. For example, a hydrocodone benzoic acid enol ester compound with high purity. For the purpose of illustration, the hydrocodone benzoic acid enol ester can have a level of impurities less than about 10% to 0.1% For example, the impurities can be, less than 10% (purity of 90%), less than 5% (purity of 95%), less than 2.0% (purity of 98%), less than 1.0% (purity of 99%), less than 0.5% (purity of 99.5%), less than 0.1% (purity of 99.9%).

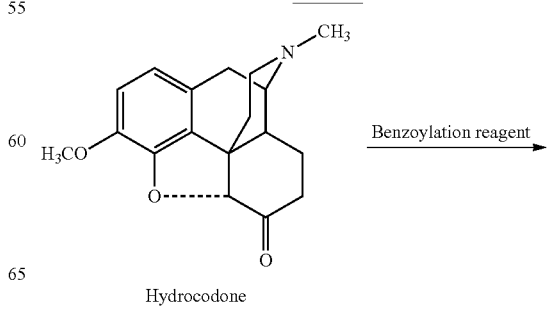

Scheme I

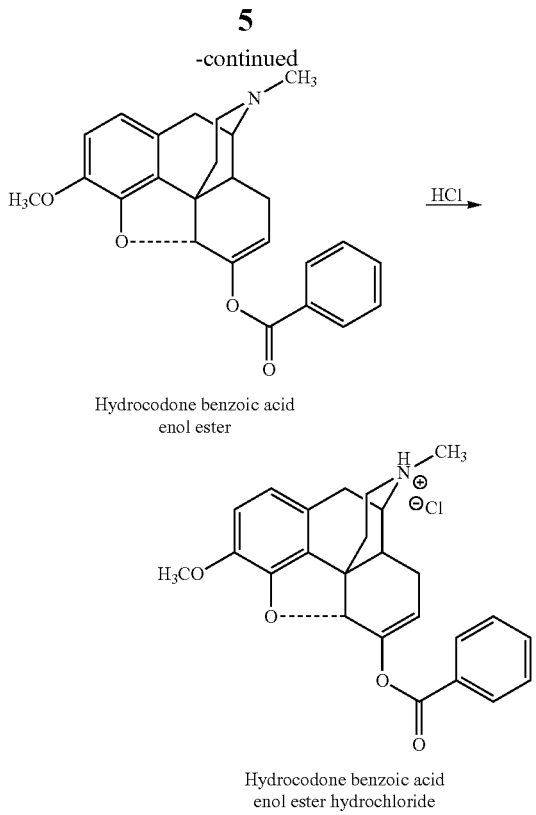

Hydrocodone benzoic acid enol ester

Hydrocodone benzoic acid enol ester hydrochloride

Synthesis.

Hydrocodone benzoic acid enol ester hydrochloride may be prepared by direct treatment of hydrocodone freebase with any benzoylating reagent, while heating the mixture, preferably in the presence of any suitable base. Hydrocodone benzoic acid enol ester hydrochloride may also be prepared by treatment of hydrocodone HX (X=Cl, Br, $HSO_4$) salts with any benzoylating reagent, while heating the mixture in any suitable solvent and any suitable base. The Hydrocodone benzoic acid enol ester HCl salt may then be formed and recrystallized. More specifically, hydrocodone or its salts may be heated in the presence of any benzoylating reagent and any suitable base. Suitable bases include pyridine, N,N-diisopropylethylamine, diazabicycloundecene, triethylamine and potassium benzoate. Some suitable solvents include toluene, dimethylformamide, N-methyl-2-pyrrolidinone, and xylenes. However, when using pyridine or another base capable of at least partially dissolving both hydrocodone and the benzoylating reagent, the reaction may be performed without an additional solvent. Any benzoylating reagent may be used, for example benzoic anhydride or benzoyl chloride.

In one embodiment, the process includes heating crude hydrocodone with benzoic anhydride and potassium benzoate in toluene or xylenes between about 80° C. and about 160° C. Once complete, the reaction may be worked up using an aqueous extraction to remove excess reagents and salts. In an alternative aspect of this embodiment, when the appropriate reaction solvent and anti-solvent are selected according to methods known in the art, the reaction may be cooled and filtered to remove most of the byproducts and reagents. Hydrocodone benzoic acid enol ester free base may be isolated in high purity at this stage.

The HCl salt may also be prepared from the filtrate solution and isolated in good purity. Optimally, an anti-solvent is added to the filtrate. Upon salt formation, hydrocodone benzoic acid enol ester crystallizes from the solution. More specifically, acetone may be used to dilute the toluene or xylenes filtrate and upon the addition of HCl, crystals of hydrocodone benzoic acid enol ester hydrochloride are obtained. Recrystallization of hydrocodone benzoic acid enol ester HCl can be accomplished from many solvents and solvent/anti-solvent combinations. Some ideal solvents are isopropyl alcohol, acetone and ethanol, with or without the addition of suitable anti-solvents.

Hydrocodone benzoic acid enol ester HCl exists in at least 6 distinct solid forms, designated herein as Forms I-V and amorphous. FIG. 1 is a scheme that depicts the general processes for converting hydrocodone benzoic acid enol ester HCl between its polymorphic forms I-V. Each polymorph has different characteristics, including solubility and stability. For example, the water solubility of Form I at 37° C. was about 24 mg/mL while Form II had water solubility of >200 mg/mL—9 times higher than the solubility of Form I. Significant water solubility differences between polymorphs could result in variation in bioavailability if mixtures are produced. Therefore, it is important to consistently produce one polymorph, preferably the one that is more stable.

Figure 2:
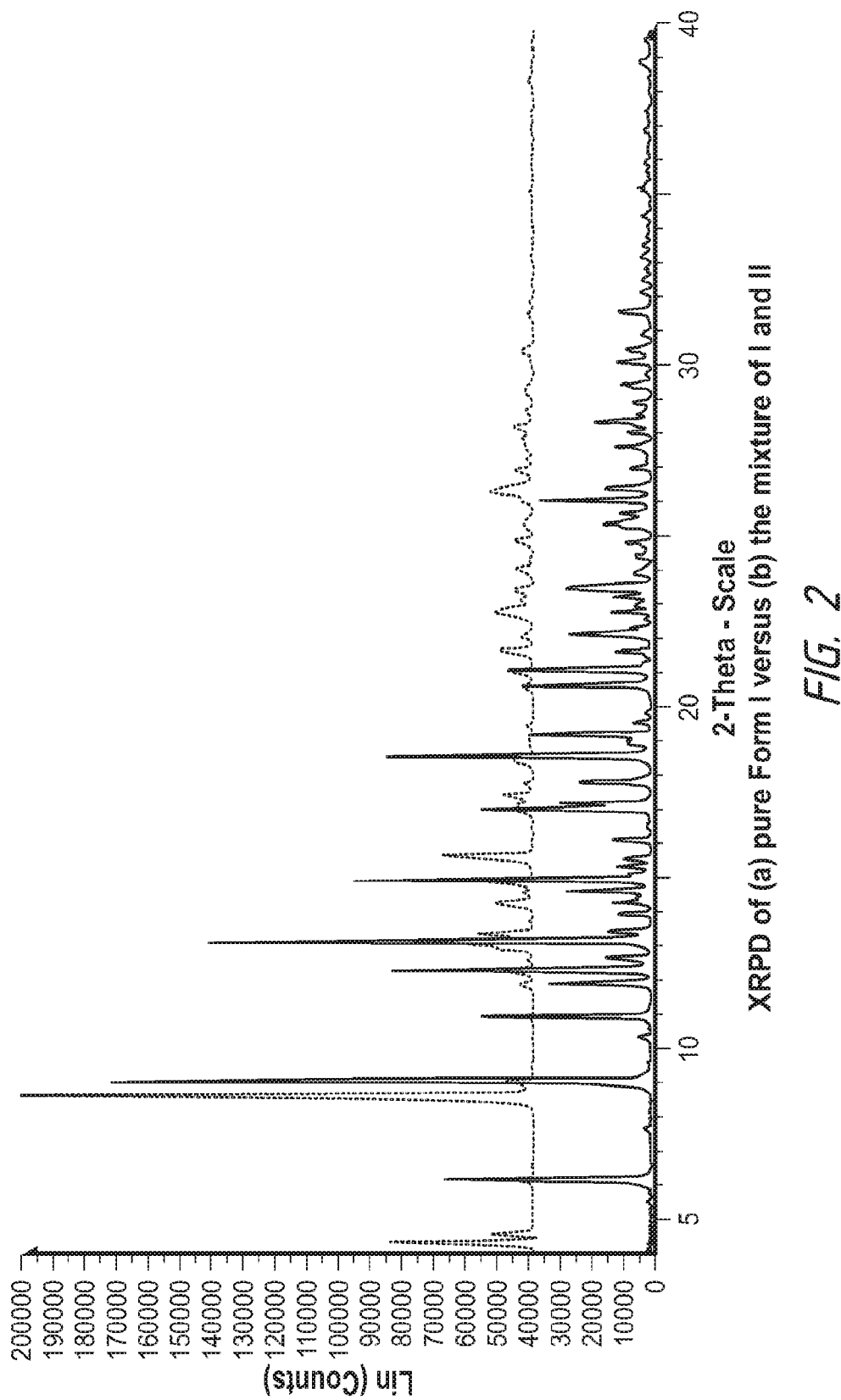
FIG. 2 shows XRPD patterns of pure hydrocodone benzoic acid enol ester HCl salt-(a) Form I and (b) mixture of Forms I and II.

Recrystallization of hydrocodone benzoic acid enol ester HCl by common procedures may produce inconsistencies in the polymorphs produced. For example, as shown in FIG. 2, recrystallization of Hydrocodone benzoic acid enol ester HCl using anhydrous isopropanol and isopropyl acetate results in a mixture comprising a mixture of polymorphs I and II.

The present disclosure describes methods of producing each polymorph in substantially pure form. Substantially pure means a minimum of 95% of the desired polymorph, preferably 98%, and more preferably 99%.

Form I.

A polymorph, designated herein as Form I, may be prepared in substantially pure form by crystallizing hydrocodone benzoic acid enol ester HCl from an organic solvent in the presence of water co-dissolved in the solvent. The water content of the solvent may vary from traces to 100%. More specifically, ethanol containing 1% water may be used as a solvent, with the addition of n-heptane as anti-solvent. Alternative solvents include but are not limited to alcohols, ethyl acetate, tBME, acetonitrile and acetone. The required water content depends on the properties of the organic solvent employed.

Figure 3:
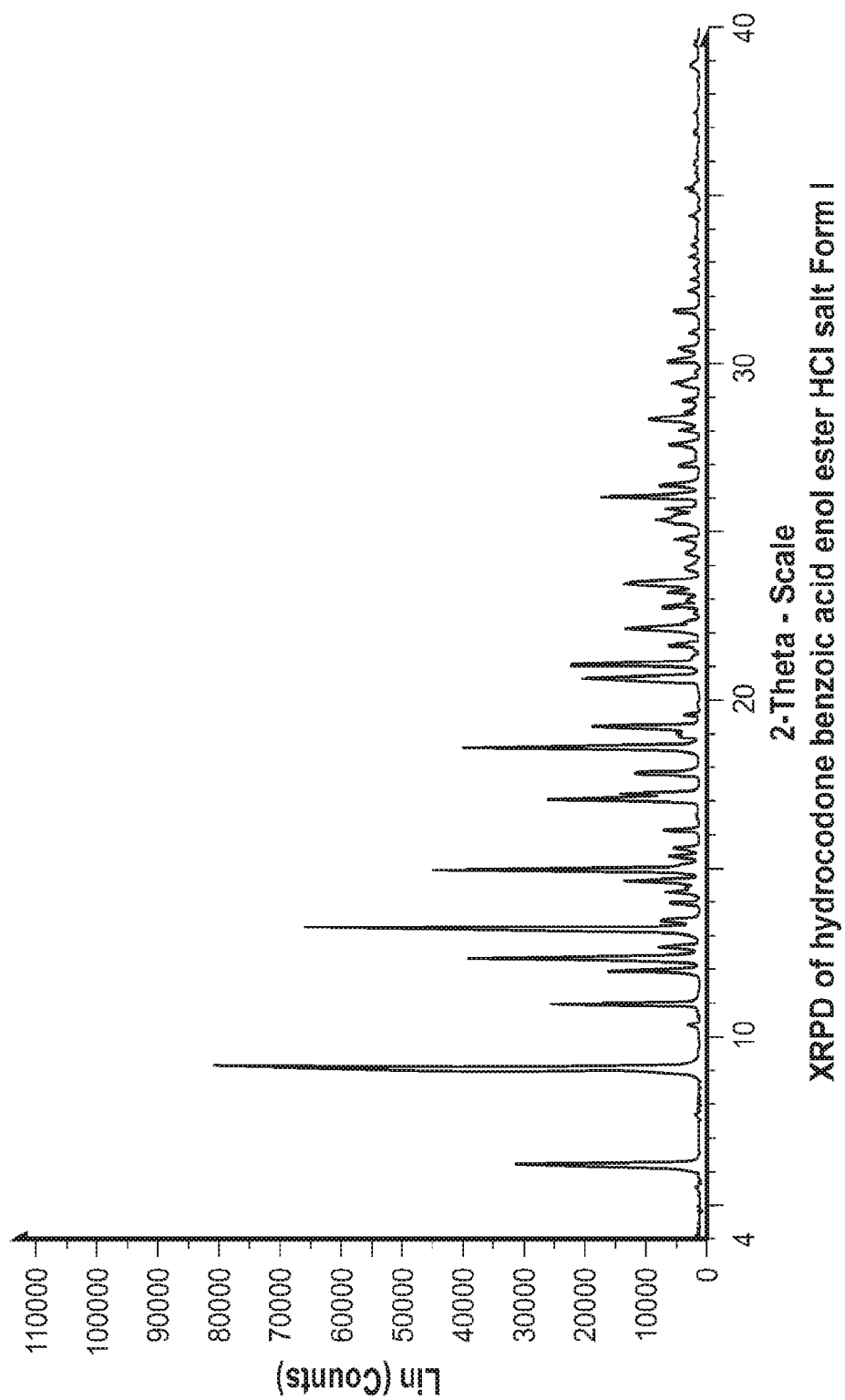
FIG. 3 shows an XRPD pattern of pure hydrocodone benzoic acid enol ester HCl salt Form I.
Figure 4:
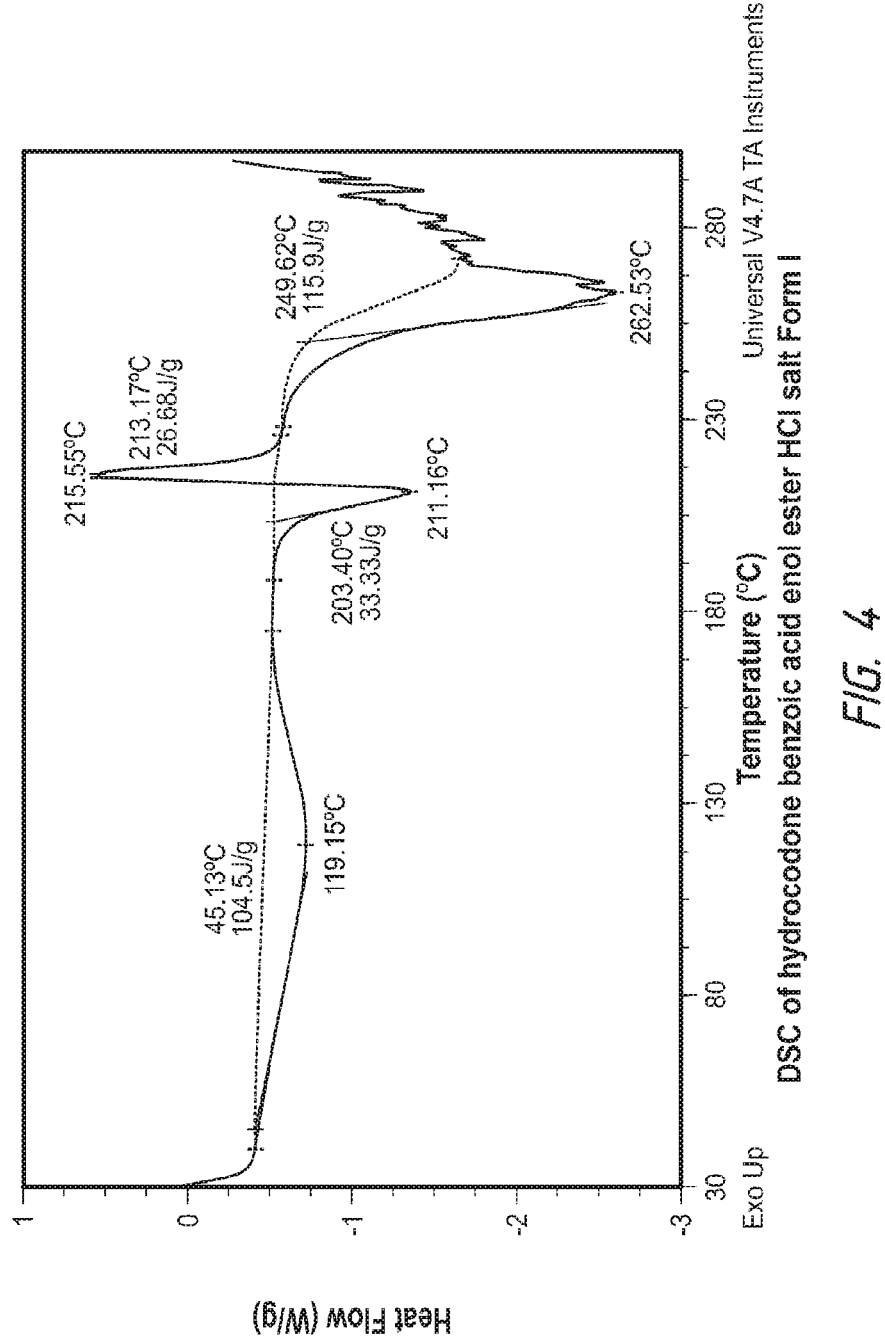
FIG. 4 shows a DSC of pure hydrocodone benzoic acid enol ester HCl salt Form I.

The XRPD pattern of Form I is presented in FIG. 3. The water content of Form I is approximately 2% by weight. This corresponds to a hemi-hydrate stoichiometry. The DSC of Form I is presented in FIG. 4. Table 1 presents selected peak positions from the XRPD and their intensity relative to the largest peak. A characteristic peak of Form I is at 2θ of 9.05°. One skilled in the art would realize that the peak position could be altered as much as ±0.2° depending on sample preparation method and XRPD instrument used for data collection.

TABLE 1

Form I XRPD peaks with intensity >10% of the largest peak

| 2θ | d spacing, A | Intensity, % |
|---|---|---|
| 6.16 | 14.34 | 38 |
| 9.05 | 9.77 | 100 |
| 10.95 | 8.07 | 31.1 |
| 11.91 | 7.42 | 18.8 |
| 12.32 | 7.18 | 47.7 |

TABLE 1-continued

Form I XRPD peaks with intensity >10% of the largest peak

| 2θ | d spacing, A | Intensity, % |
|---|---|---|
| 13.16 | 6.72 | 81.8 |
| 14.60 | 6.06 | 15.6 |
| 14.94 | 5.92 | 54.9 |
| 17.04 | 5.20 | 31.3 |
| 17.23 | 5.14 | 13.5 |
| 17.80 | 4.98 | 13.5 |
| 18.57 | 4.77 | 48.6 |
| 19.18 | 4.62 | 22.4 |
| 20.66 | 4.30 | 23.9 |
| 21.10 | 4.21 | 26.6 |
| 22.15 | 4.01 | 15 |
| 23.50 | 3.78 | 15.7 |
| 26.07 | 3.41 | 20.5 |
| 28.39 | 3.14 | 10.4 |

Form II.

A polymorph, designated herein as Form II, may be produced in substantially pure form by crystallizing any other form of hydrocodone benzoic acid enol ester HCl from an organic solvent system that is substantially free of water. Substantially free of water means a water content of less than 0.2 percent by volume and more preferably less than 0.1 percent by volume. Substantially pure Form II means a minimum of 95% of Form II, or preferably 98% and more preferably 99%.

Figure 5:
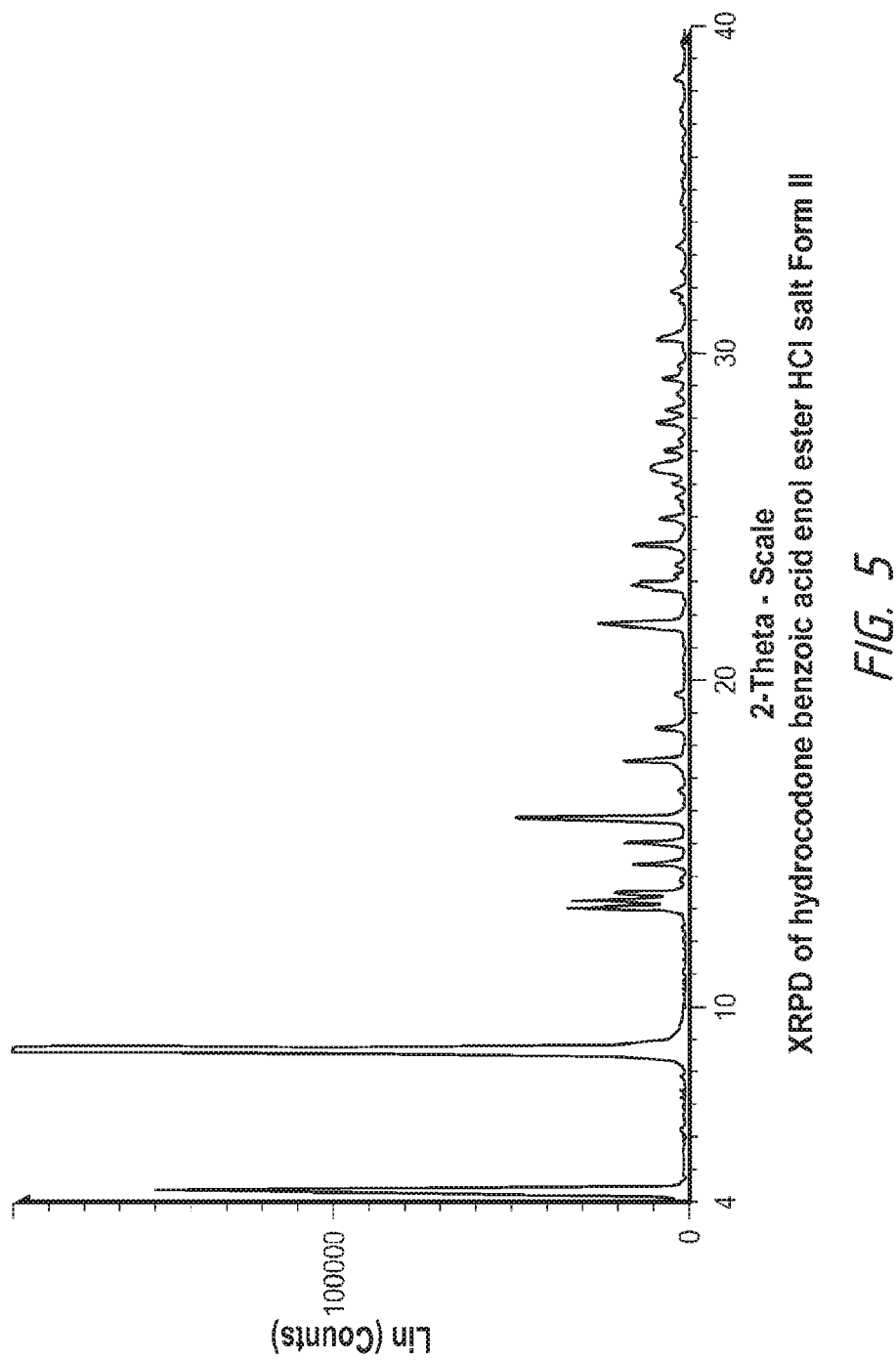
FIG. 5 shows an XRPD pattern of pure hydrocodone benzoic acid enol ester HCl salt Form II.
Figure 6:
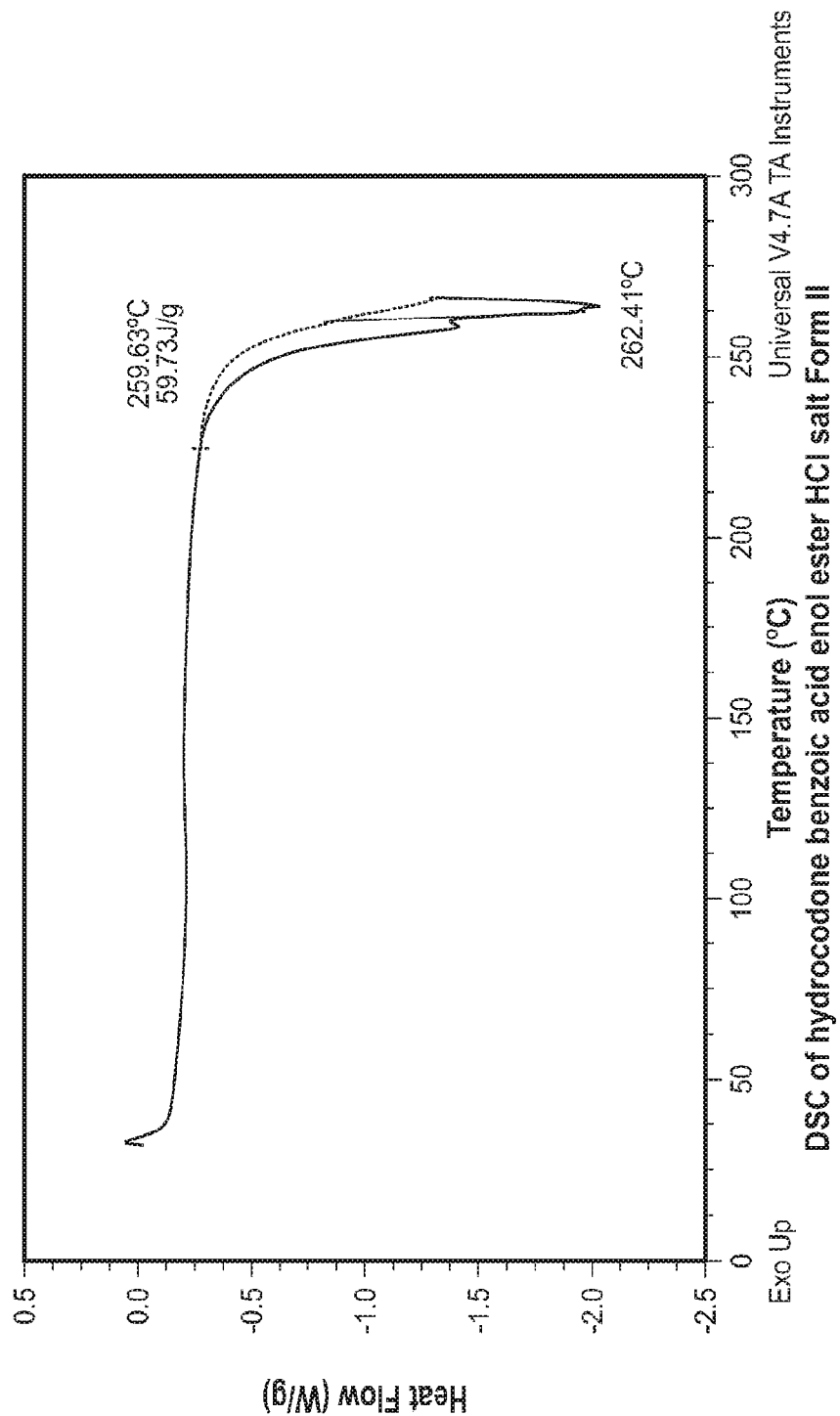
FIG. 6 shows a DSC of pure hydrocodone benzoic acid enol ester HCl salt Form II.

The XRPD pattern of Form II is presented in FIG. 5. The DSC of Form II is presented in FIG. 6. Table 2 presents selected peak positions from the XRPD and their intensity relative to the biggest peak. A characteristic peak of Form II is at 2θ of 4.31°. One skilled in the art will realize that the peak position may be altered as much as ±0.2° depending on sample preparation method and XRPD instrument used for data collection.

TABLE 2

Form II XRPD peaks with intensity >1% of the largest peak

| 2θ | d spacing, A | Intensity, % |
|---|---|---|
| 4.31 | 20.48 | 20.6 |
| 8.62 | 10.25 | 100 |
| 12.95 | 6.83 | 4.6 |
| 13.19 | 6.71 | 4.4 |
| 13.42 | 6.59 | 2.8 |
| 14.33 | 6.17 | 2 |
| 14.97 | 5.91 | 2.4 |
| 15.72 | 5.63 | 6.6 |
| 17.48 | 5.07 | 2.4 |
| 18.47 | 4.80 | 1.2 |
| 21.73 | 4.09 | 3.4 |
| 22.92 | 3.88 | 2.1 |
| 24.15 | 3.68 | 2 |
| 24.98 | 3.56 | 1 |
| 26.41 | 3.37 | 1.3 |
| 26.53 | 3.36 | 1.4 |
| 26.62 | 3.34 | 1.3 |
| 27.93 | 3.19 | 1.1 |
| 30.46 | 2.93 | 1.17 |

Form III.

A novel polymorph, designated as Form III, may be prepared in substantially pure form by heating Form I to any temperature between 210° C. to 230° C., preferably 215-225° C. and more preferably 217° C. One skilled in the art could perform this heating operation in a different equipment, e.g. a heating cell, while giving enough time at the high temperature to achieve complete formation of Form II. Substantially pure Form III means a minimum of 95% of Form III, or preferably 98% and more preferably 99%.

Figure 7:
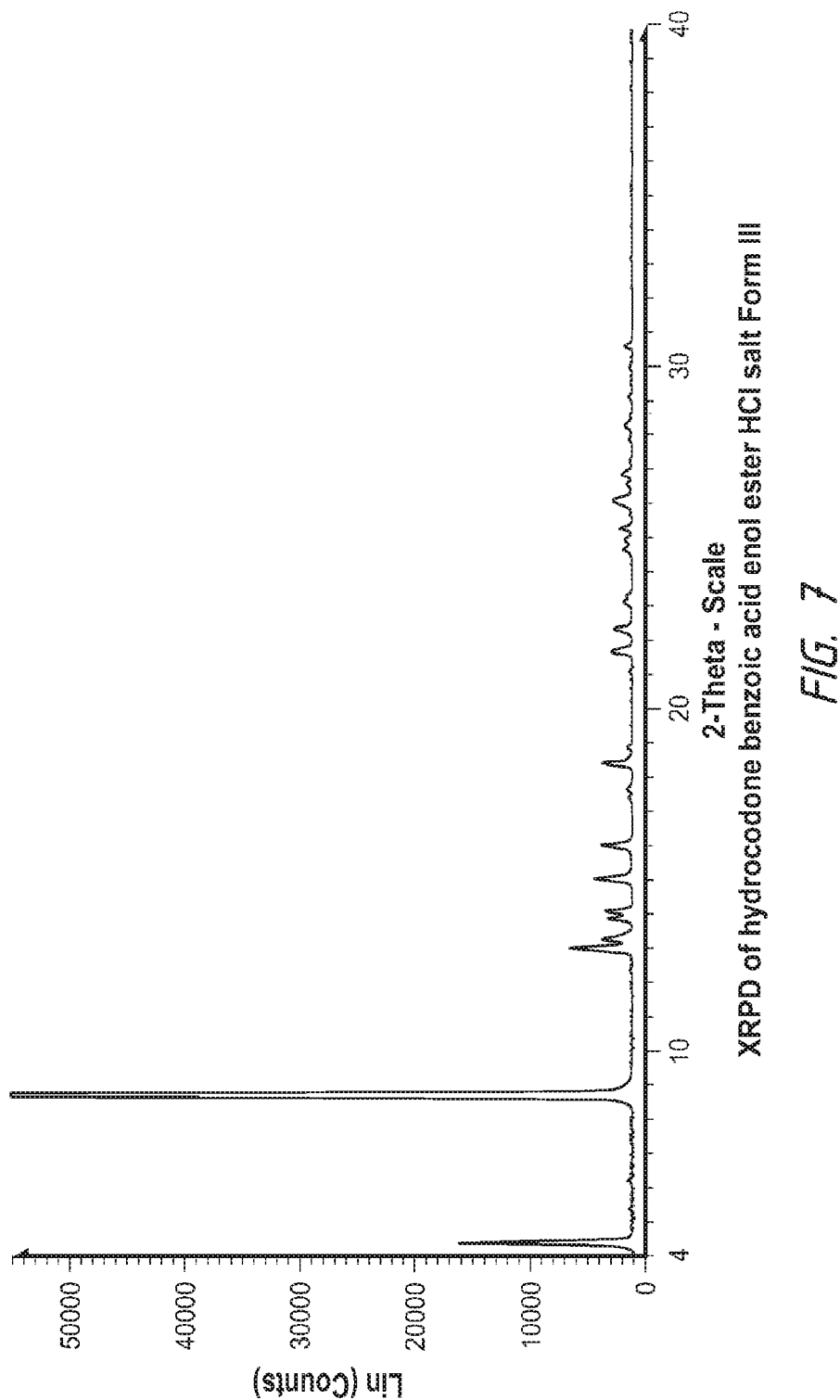
FIG. 7 shows an XRPD pattern of pure hydrocodone benzoic acid enol ester HCl salt Form III.
Figure 8:
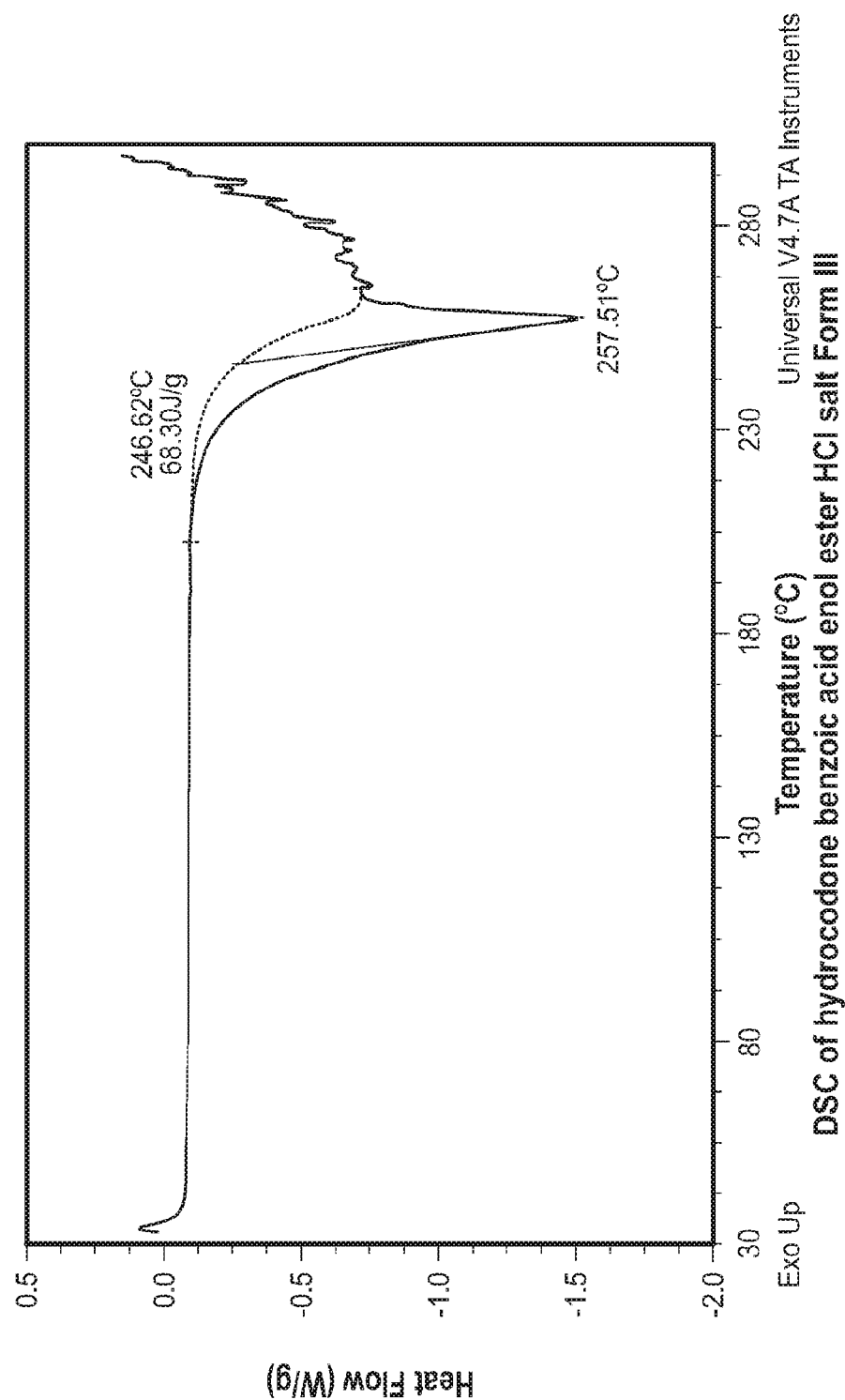
FIG. 8 shows a DSC of pure hydrocodone benzoic acid enol ester HCl salt Form III.

The XRPD pattern of Form III is presented in FIG. 7. The DSC of Form III is presented in FIG. 8. Table 3 presents selected peak positions from the XRPD and their intensity relative to the largest peak. A characteristic peak of Form III is at 2θ of 13.01°. One skilled in the art will realize that the peak position may differ from the listed positions by as much as ±0.2° depending on sample preparation method and XRPD instrument used for data collection.

TABLE 3

Form III XRPD peaks with intensity >3% of the largest peak

| 2θ | d spacing, A | Intensity, % |
|---|---|---|
| 4.35 | 20.28 | 21.1 |
| 8.68 | 10.18 | 100 |
| 13.01 | 6.80 | 8.6 |
| 13.27 | 6.67 | 4.7 |
| 13.86 | 6.39 | 4.1 |
| 14.06 | 6.29 | 4.5 |
| 15.05 | 5.88 | 5.6 |
| 16.02 | 5.53 | 4.8 |
| 18.40 | 4.82 | 4.8 |
| 21.72 | 4.09 | 3.5 |
| 22.38 | 3.97 | 3.4 |
| 26.14 | 3.41 | 3.6 |

Form IV.

A novel polymorph, designated as Form IV, may be prepared in substantially pure form by exposing Form II to a relative humidity of 75-100% for a period of two weeks. Preferably, the relative humidity is in the range of 75-100%, more preferably it is in the range 85-95% and most preferably the relative humidity is 90%. Substantially pure Form IV means a minimum of 95% of Form IV, or preferably 98% and more preferably 99%.

Figure 9:
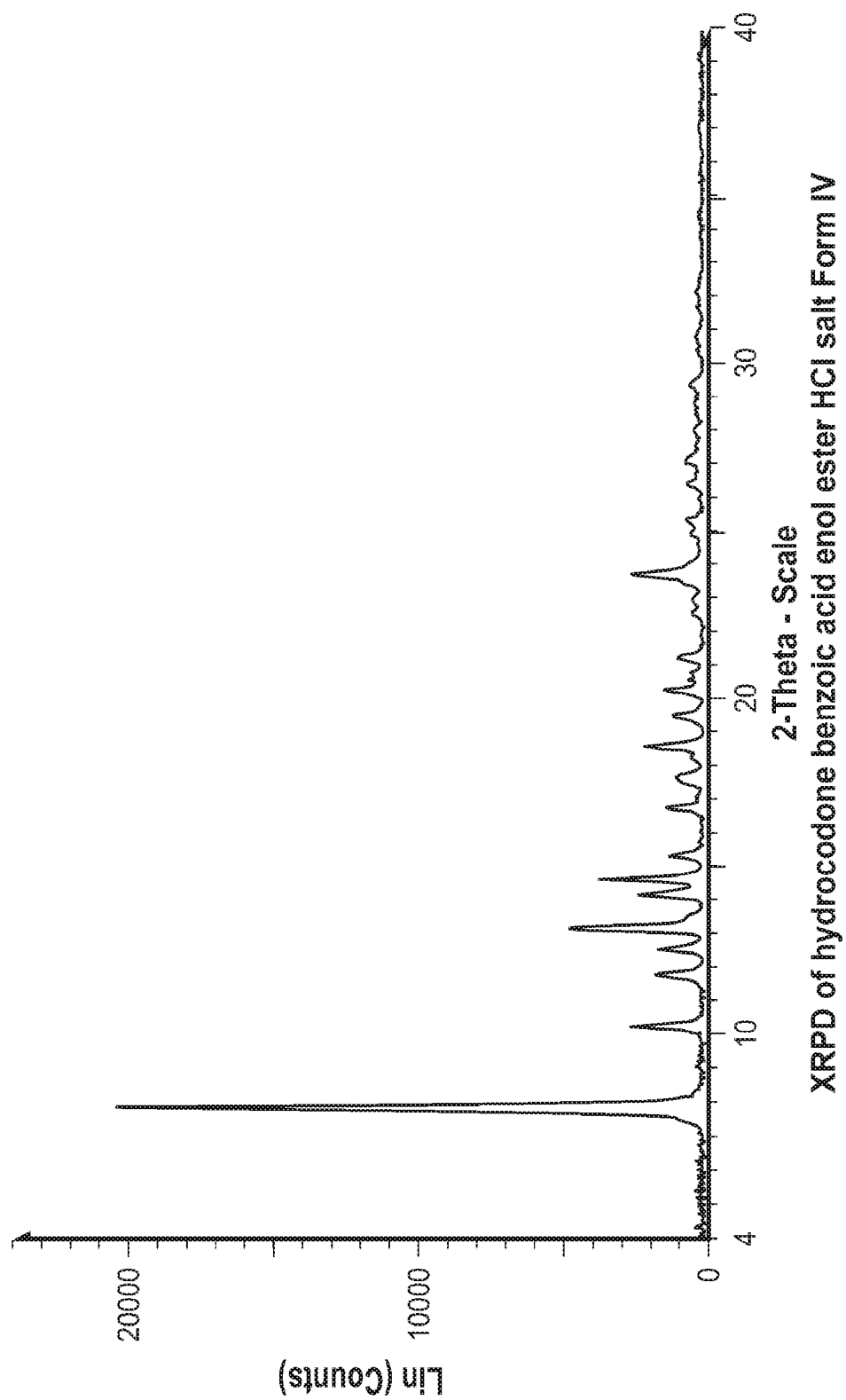
FIG. 9 shows an XRPD pattern of pure hydrocodone benzoic acid enol ester HCl salt Form IV.
Figure 10:
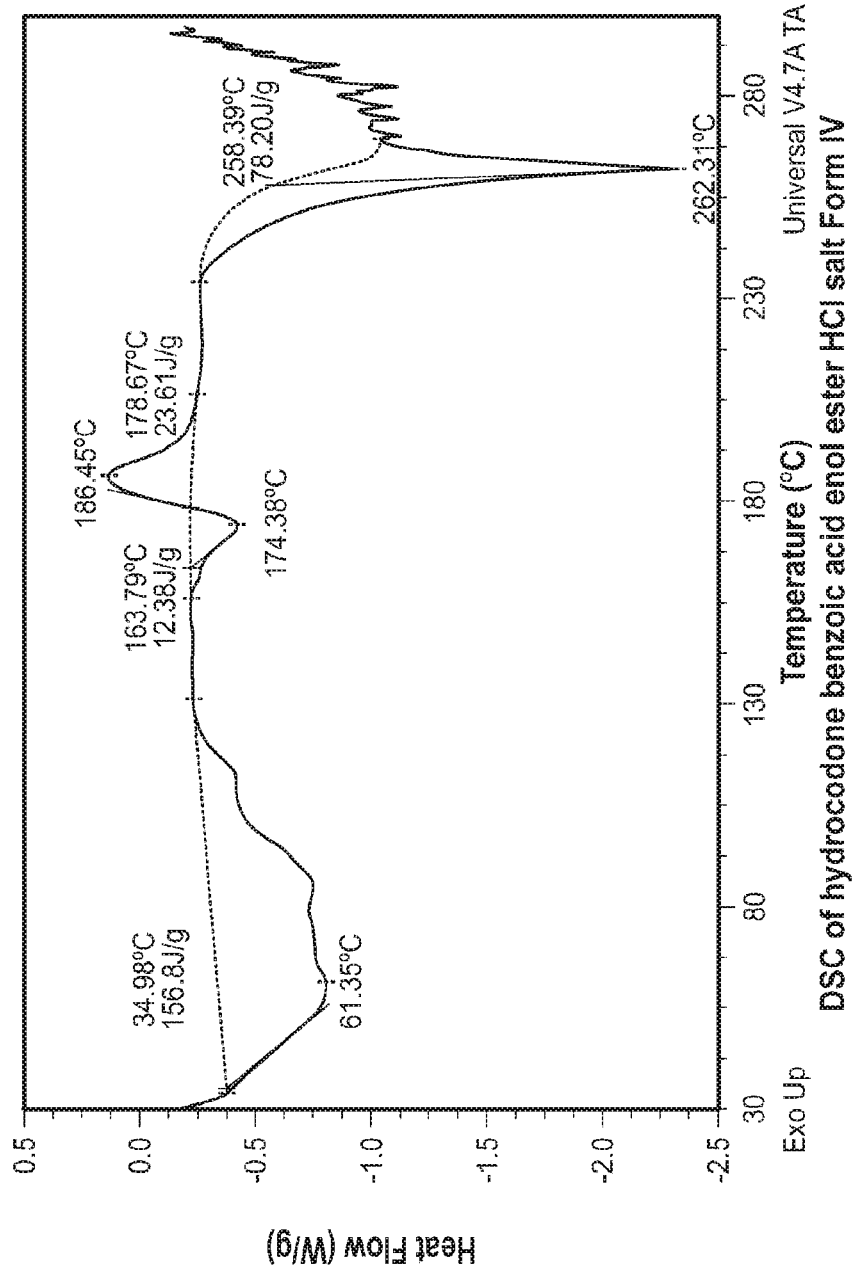
FIG. 10 shows a DSC of pure hydrocodone benzoic acid enol ester HCl salt Form IV.

The XPRD pattern of Form IV is presented in FIG. 9. The DSC of Form IV is presented in FIG. 10. Table 4 presents selected peak positions in the XRPD and their intensity relative to the largest peak. A characteristic peak of Form IV is at 2θ of 7.87°. One skilled in the art will realize that the peak position could be altered as much as ±0.2° depending on sample preparation method and XRPD instrument used for data collection.

TABLE 4

Form IV XRPD peaks with intensity >4% of the largest peak

| 2θ | d spacing, A | Intensity, % |
|---|---|---|
| 7.87 | 11.23 | 100 |
| 10.27 | 8.61 | 12.1 |
| 11.82 | 7.48 | 8.1 |
| 12.56 | 7.04 | 7.5 |
| 13.18 | 6.71 | 22.6 |
| 14.19 | 6.24 | 10.8 |
| 14.65 | 6.04 | 17.6 |
| 15.34 | 5.77 | 5.8 |
| 16.77 | 5.28 | 6.2 |
| 17.67 | 5.01 | 4.4 |
| 18.58 | 4.77 | 9.9 |
| 19.50 | 4.55 | 5.2 |
| 20.30 | 4.37 | 6.2 |
| 21.31 | 4.17 | 4 |

Form V.

A novel polymorph, designated as Form V, may be prepared in substantially pure form by exposing Form III to a relative humidity of 75-100% for a period of two weeks.

Preferably, the relative humidity is in the range of 75-100%, more preferably it is in the range 85-95% and most preferably the relative humidity is 90%. Substantially pure Form II means a minimum of 95% of Form II, or preferably 98% and more preferably 99%.

Figure 11:
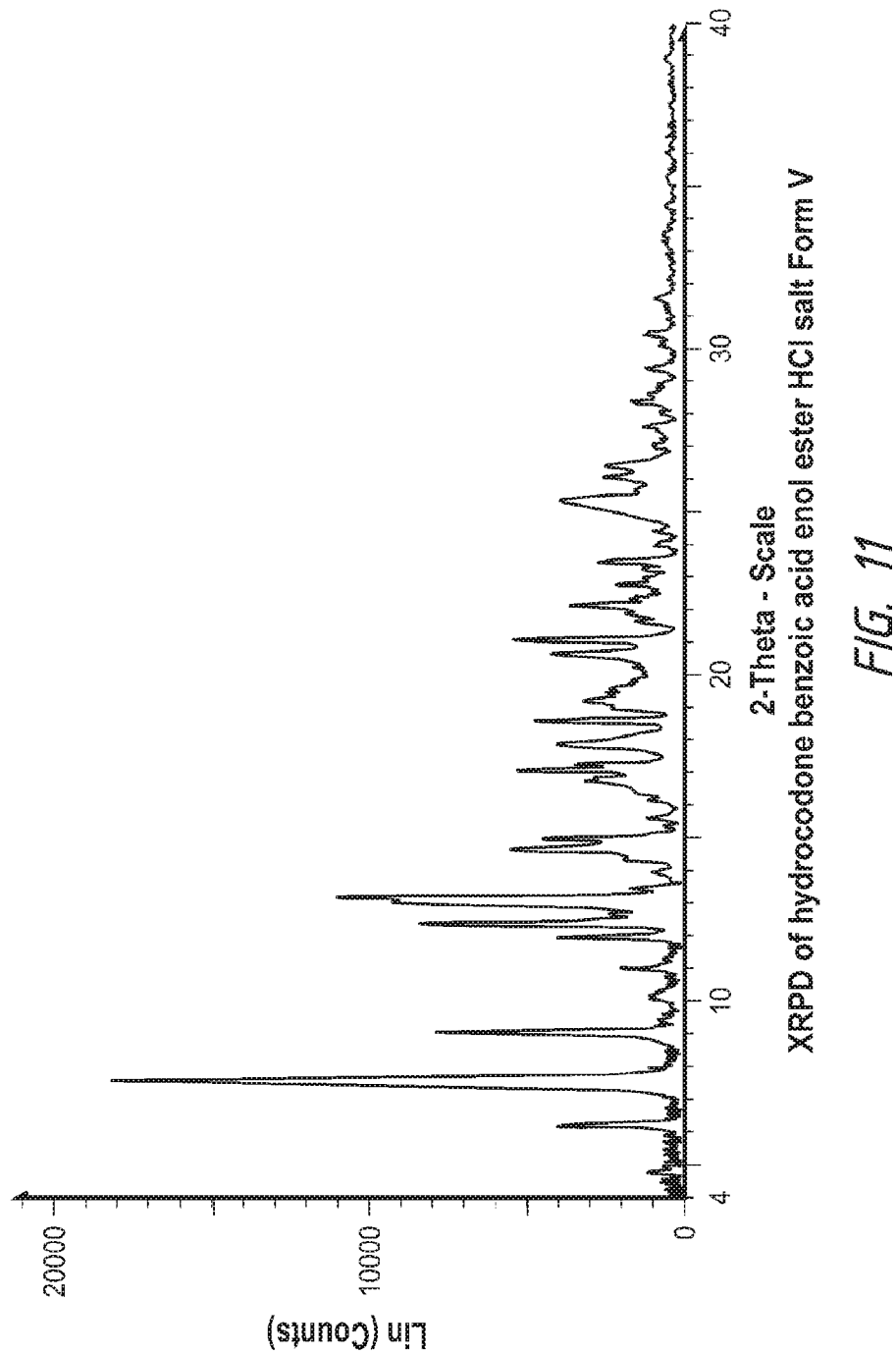
FIG. 11 shows an XRPD pattern of pure hydrocodone benzoic acid enol ester HCl salt Form V.
Figure 12:
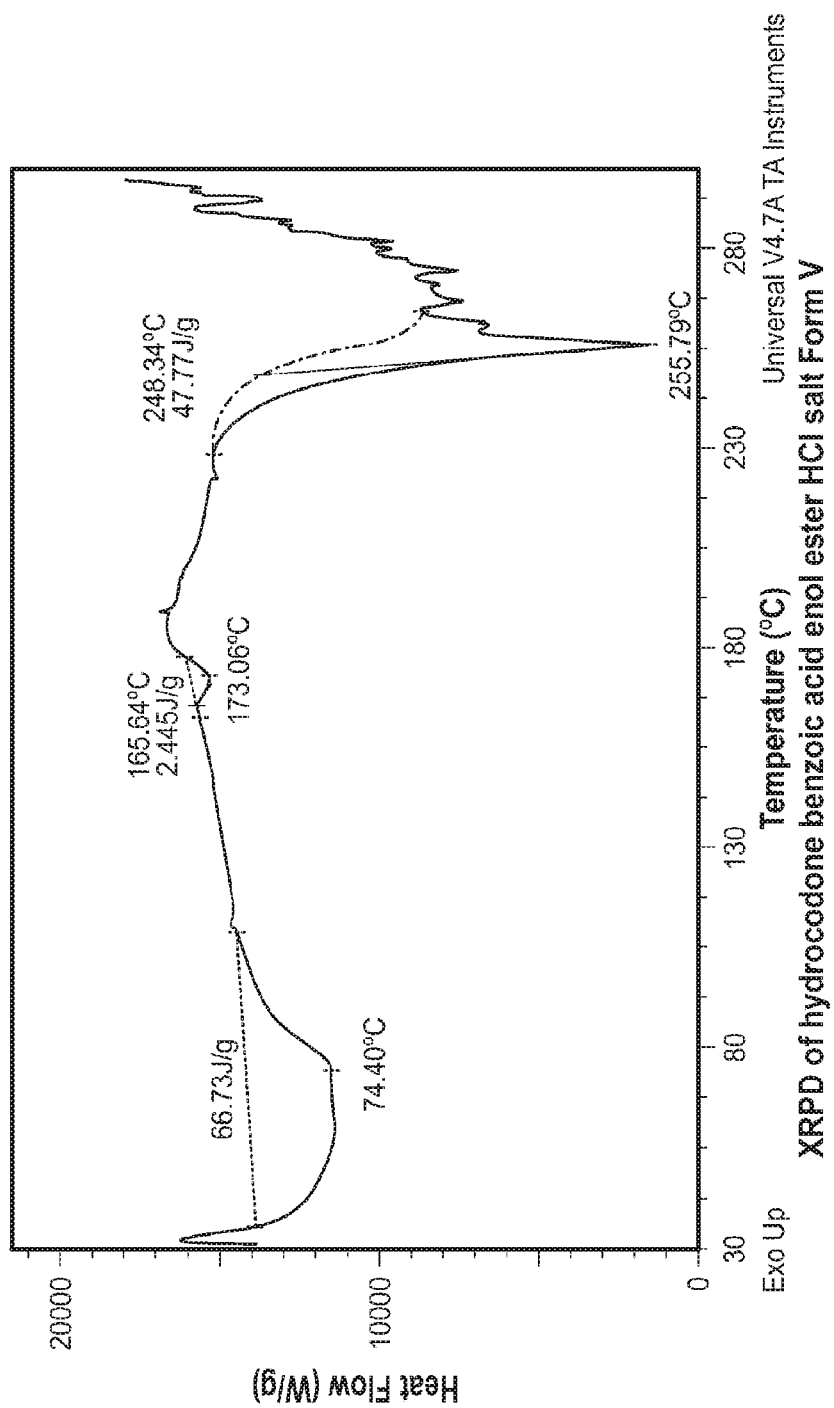
FIG. 12 shows a DSC of pure hydrocodone benzoic acid enol ester HCl salt Form V.

The XRPD pattern of Form V is presented in FIG. 11. The DSC is presented in FIG. 12. Table 5 presents selected peak position from the XRPD and their intensity relative to the largest peak. A characteristic peak of Form V is at 2θ of 7.50°. One skilled in the art will realize that the peak position could be altered as much as ±0.2° depending on sample preparation method and XRPD instrument used for data collection.

TABLE 5

Form V XRPD peaks with intensity >10% of the largest peak

| 2θ | d spacing, A | Intensity, % |
| --- | --- | --- |
| 6.17 | 14.31 | 21.4 |
| 7.50 | 11.78 | 100 |
| 9.04 | 9.77 | 44.2 |
| 10.96 | 8.07 | 10.3 |
| 11.93 | 7.42 | 22.3 |
| 12.34 | 7.17 | 47 |
| 12.64 | 6.99 | 12.8 |
| 13.13 | 6.74 | 60.8 |
| 14.34 | 6.17 | 10.6 |
| 14.62 | 6.05 | 31.1 |
| 14.93 | 5.93 | 25 |
| 16.73 | 5.29 | 17.3 |
| 17.04 | 5.20 | 29.8 |
| 17.22 | 5.15 | 18.6 |
| 17.81 | 4.98 | 22.4 |
| 18.59 | 4.77 | 26.4 |
| 18.98 | 4.67 | 13.2 |
| 19.19 | 4.62 | 18 |
| 19.52 | 4.55 | 12.4 |
| 20.67 | 4.29 | 23.4 |
| 21.10 | 4.21 | 30.6 |
| 21.91 | 4.05 | 10.1 |
| 22.15 | 4.01 | 20.1 |
| 22.82 | 3.89 | 11.7 |
| 23.49 | 3.78 | 15.2 |
| 25.03 | 3.56 | 12.5 |
| 25.37 | 3.51 | 21.9 |
| 26.09 | 3.41 | 14.6 |
| 26.43 | 3.37 | 13.8 |

Amorphous Form.

An amorphous form of hydrocodone benzoic acid enol ester may be prepared in substantially pure form by dissolving the hydrocodone benzoic acid enol ester in an organic solvent, then evaporating the solvent in an oven. The solvent may be any organic solvent that dissolves hydrocodone benzoic acid enol ester, including methanol, trifluoroethanol, and acetic acid.

Figure 13:
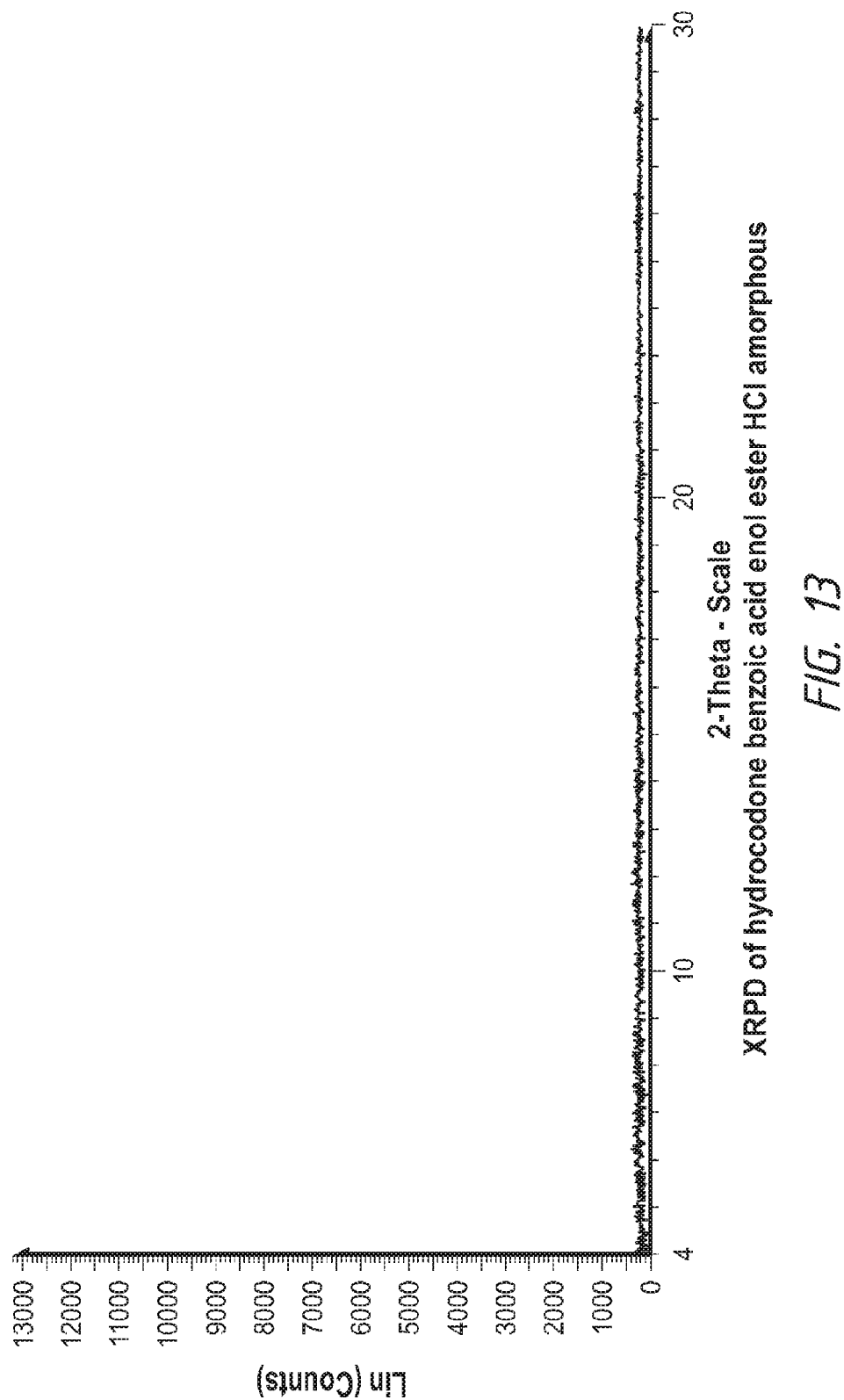
FIG. 13 shows an XRPD pattern of pure amorphous hydrocodone benzoic acid enol ester HCl salt.
Figure 14:
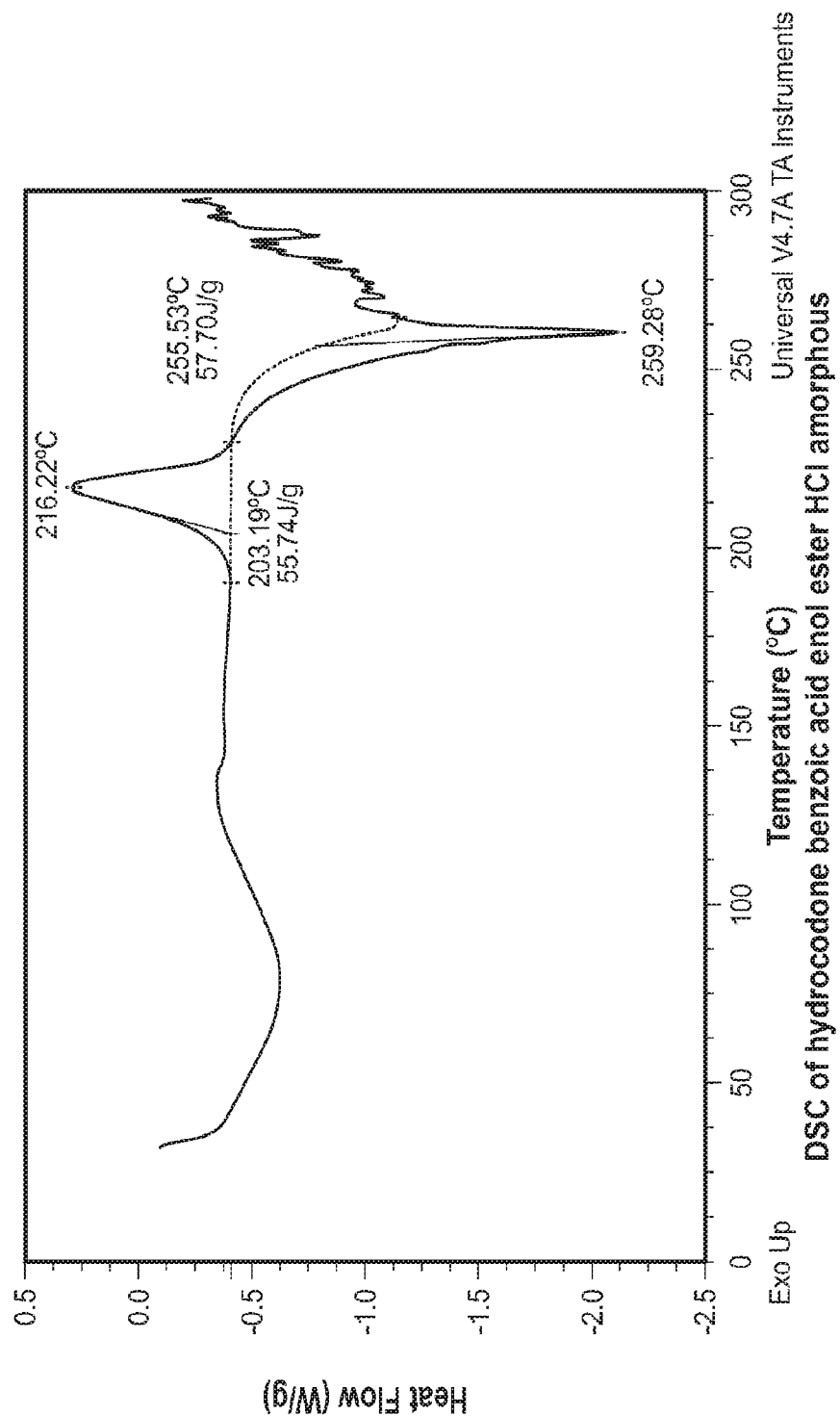
FIG. 14 shows a DSC of pure amorphous hydrocodone benzoic acid enol ester HCl salt.

The XRPD pattern of the amorphous form is presented in FIG. 13. The DSC of the amorphous form is presented in FIG. 14. Upon heating of amorphous solid in DSC, an endothermic peak with maximum at about 216° C. was observed.

EXAMPLES

Example 1: Synthesis of Hydrocodone Benzoic Acid Enol Ester Hydrochloride Free Base A mixture of crude hydrocodone freebase (1 eq.), benzoic anhydride (2.5 eq.), and potassium benzoate (1.0 eq.) in toluene (1.8 vol. to hydrocodone) was stirred and heated at 129±3° C. until >98% conversion of hydrocodone to hydrocodone benzoic acid enol ester by HPLC (~24 hr.). The mixture was cooled to room temperature and diluted with toluene (0.8 vol.) then further cooled to 5° C. The resulting mixture was filtered to remove potassium benzoate and benzoic acid. The cake was washed with toluene (2×0.75 vol.). The filtrate was washed with NaHCO$_3$ solution (5%, 4 vol.) and brine (10%, 2 vol.). The organic layer was dried with sodium sulfate (2×). The mixture was filtered and the cake was washed with toluene. The filtrate was concentrated to give oily residue of hydrocodone benzoic acid enol ester.

Example 2: Synthesis of Hydrocodone Benzoic Acid Enol Ester Hydrochloride

A mixture of crude hydrocodone freebase (1 eq.), benzoic anhydride (2.5 eq.), and potassium benzoate (1.0 eq.) in toluene (1.8 vol. to hydrocodone) was stirred and heated at 129±3° C. until >98% conversion of hydrocodone to hydrocodone benzoic acid enol ester by HPLC (~24 hr.). The mixture was cooled to room temperature and diluted with toluene (0.8 vol.) then further cooled to 5° C. The resulting mixture was filtered to remove potassium benzoate and benzoic acid. The cake was washed with toluene (2×0.75 vol.). The filtrate was diluted with acetone (6 vol.) and cooled to 5±2.5° C. with agitation. Concentrated HCl (1.1±0.05 equivalents) was added and the resulting mixture was stirred at 5±2.5° C. for 2 hr. The solid suspension was filtered and the cake was washed with acetone (2×1 vol.). The solid was dried on the filter to give crude hydrocodone benzoic acid enol ester hydrochloride in 88% yield and 98.9% AUC purity. Crude hydrocodone benzoic acid enol ester was dissolved in ethanol (6.0 vol.) at 65 to 70° C. DI water (1% v/v with respect to total amount of EtOH) was added and the mixture was allowed to cool to 50±5° C. and held for 30 to 60 minutes after crystal growth was noticed. n-Heptane (3 vol.) was added at 50±5° C. The mixture was cooled to room temperature over approximately 1 hr. and then further cooled to 5±2.5° C. and stirred for 1.5 hr. The solid mixture was filtered and the crystalline product cake was rinsed with a mixture of ethanol and n-heptane. The cake was dried under vacuum to give hydrocodone benzoic acid enol ester hydrochloride as Form I in 93.5% recovery, >99.9% AUC purity, 82.5% overall yield from hydrocodone.

Example 3: Synthesis of Hydrocodone Benzoic Acid Enol Ester HC Salt (Form 1) from the Corresponding Free Base To 475 mg of hydrocodone benzoic acid enol ester were added 4.75 mL of Acetone:Toluene (1.5:1 vol ratio) at room temperature, which resulted in a solution. Then, 1.03 eq. of concentrated HCl (37.5 wt %) were slowly added to the freebase solution. Precipitation started during the addition. After completion of acid addition, the slurry was stirred for about 30 minutes and filtered. The cake was washed with about 0.5 mL acetone and then dried. The dry solid was substantially pure Form I.

In example 3, other organic solvents such as but not limited to alcohols, tBME and ethyl acetate could be used. Instead of adding solvent to freebase, the freebase could be added to solvent. The temperature of acid addition could be in the range of 0° C. to 60° C., preferably 10° C. to 40° C. and more preferably 20° C. to 30° C.

Example 4: Form I Recrystallization

To 158 mg of HCl salt Form I was added 7.8 volumes of Ethanol and the mixture heated to 65° C. to achieve dissolution. The solution was then cooled to 50° C. followed by addition of 12.2 µL water. When a crystal bed was achieved, 2.7 volumes of heptane were added over about 30 minutes followed by cooling to 20-25° C. Filtration and drying resulted in Form I (84% yield) with a chemical purity of 99+%.

In example 4, ethanol could be replaced with other organic solvents such as but not limited to other alcohols and acetone. Instead of adding solvent to the salt, the salt could be added to the solvent. The temperature of water addition could be in the range of 0° C. to 60° C., preferably 30° C. to 55° C. and more preferably 45° C. to 50° C. The water quantity could be in the range of 0.2% to 15 vol % with respect to organic solvent, preferably 0.3-5% and more preferably 0.8-1.2%. Alternatively, seeds of Form I could be added to promote crystallization after water addition. Heptane volume could be in the range of 0-15 volumes, preferably 1-5 volumes and more preferably 2-3 volumes. The starting solid of this example could be Form I or any other polymorphs of hydrocodone benzoic acid enol ester HCl.

Example 5: Form I Recrystallization

To 130 mg of HCl salt Form I were added 7.8 volumes of Ethanol and heated to 65° C. to achieve dissolution. The solution was then cooled to 50° C. followed by addition of 10 µL water. Within 30 minutes a crystal bed was achieved. The mixture was cooled to 20° C. to 25° C., filtered, and dried which resulted in Form I (80% yield) and a chemical purity of 99+%.

In example 5, ethanol could be replaced with other organic solvents such as but not limited to other alcohols and acetone. Instead of adding solvent to the salt, the salt could be added to the solvent. The temperature of water addition could be in the range of 0° C. to 60° C., preferably 30° C. to 55° C. and more preferably 45° C. to 50° C. The water quantity could be in the range of 0.2% to 15 vol % with respect to organic solvent, preferably 0.3-5% and more preferably 0.8-1.2%. Alternatively, seeds of Form I could be added to promote crystallization after water addition. The starting solid of this example could be Form I or any other polymorphs of hydrocodone benzoic acid enol ester HCl.

Example 6: Synthesis of Hydrocodone Benzoic Acid Enol Ester HCl Salt (Form II)

To about 118 mg of Form I were added 12.3 volumes of anhydrous isopropanol and 13.4 volumes of anhydrous isopropyl acetate added and the slurry was heated to reflux to achieve complete dissolution. The solution was cooled to about 20° C. over about 3 hrs. Nucleation was observed at about 60° C. The slurry was filtered at about 20° C. and the product was dried. The resulting solid was substantially pure Form II with 67% yield.

Example 7: Synthesis of Hydrocodone Benzoic Acid Enol Ester HC Salt (Form III)

Hydrocodone benzoic acid enol ester HCl salt (Form I) was heated to 217° C. in DSC followed by cooling to room temperature which resulted in substantially pure Form III by XRPD analysis.

Example 8: Synthesis of Hydrocodone Benzoic Acid Enol Ester HCl Salt (Form IV)

Hydrocodone benzoic acid enol ester HCl salt (Form II) was exposed to humidity of more than 90% at room temperature for two weeks, which resulted in Form IV confirmed by XRPD.

Example 9: Synthesis of Hydrocodone Benzoic Acid Enol Ester HCl Salt (Form V)

Hydrocodone benzoic acid enol ester HCl salt (Form III) was exposed to humidity of more than 90% at room temperature for two weeks, which resulted in Form V confirmed by XRPD.

Example 10: Synthesis of Hydrocodone Benzoic Acid Enol Ester HCl Salt (Amorphous Form)

64 mg of Hydrocodone benzoic acid enol ester HCl salt was dissolved in 1 mL of methanol. The solvent was evaporated in the oven temperature of 50° C. and under vacuum. The resulting solid was amorphous by XRPD.

Example 11: Slurry Stability Studies

A number of experiments were performed to map out the relative stability of Forms I to V. Prior to the relative stability tests, the solids of Forms I, II and III were dried in the oven to remove surface water. Table 6 shows the results of these slurries. It was found that Form I is always the most stable in water or organic solvents that contain water. However, in anhydrous organic solvents, Form II is the more stable one, especially at higher temperatures. Therefore, Form I was selected as the most viable form for development.

TABLE 6

Relative stability of various forms

| Solvent | Starting Form | After 1 day slurry | | After 10 days slurry | |
| --- | --- | --- | --- | --- | --- |
| | | 25° C. | 50° C. | 25° C. | 50° C. |
| Water | I + II + III | I | I | I | I |
| Water | I + IV + V | I | I | I | I |
| IPA | I + II + III | I + II | I + II | I | II |
| Acetonitrile | I + II + III | I + traces of II | II | I | I |

Example 12: Grinding Stability Studies

Form I was exposed to dry and solvent drop grinding using mortar and pestle. This test mimics shear stresses that a crystal polymorph could be exposed to during commercial formulation. Table 7 illustrates the grinding results.

TABLE 7

Wet and dry grinding of Form I - 5 minutes of manual grinding

| Starting Form | Conditions | Resulting Form |
|---|---|---|
| I | Dry grinding | I |
| I | Wet grinding- ~0.3X vol water | I |
| I | Wet grinding- ~0.5X vol IPA | I |

Example 13: Humidity Stability Studies

The stability of various forms of hydrocodone benzoic acid enol ester hydrochloride was evaluated under high humidity (RH>90% at room temperature) conditions. Form I was stable for at least two weeks. Form II was hygroscopic and unstable, and converted to Form IV. Form III was hygroscopic and unstable, and converted to Form V.

The invention claimed is:

1. A process for the preparation of the following compound:

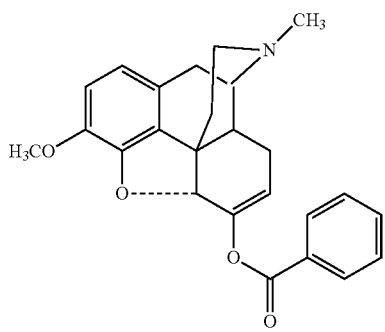

wherein the compound is a polymorphic form of hydrocodone benzoic acid enol ester, wherein the polymorphic form is Form I and Form I has an x-ray powder diffraction pattern comprising peaks at about the following 2θ values: 9.05, 12.32, 13.16, 14.94, and 18.57 comprising the steps of:
 (a) preparing a mixture comprising hydrocodone free base and either benzoic anhydride or benzoyl chloride and,
 (b) heating the mixture to a temperature in the range of about 80° C. to about 160° C.

2. The process of claim 1 further comprising the step of adding concentrated hydrochloric acid to the mixture to produce a compound having a following structure:

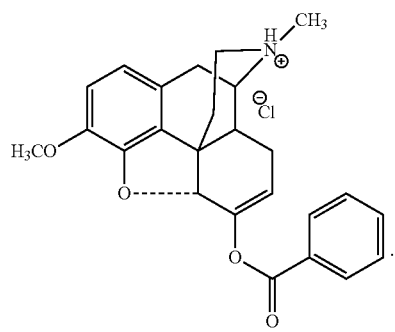

3. A pharmaceutical composition comprising a therapeutically effective amount of the compound prepared according to the process of claim 1 and a pharmaceutically acceptable excipient.

4. A pharmaceutical composition comprising a therapeutically effective amount of the compound prepared according to the process of claim 2 and a pharmaceutically acceptable excipient.

5. The process of claim 1, wherein the mixture further comprises a suitable organic solvent.

6. The process of claim 5, wherein the suitable organic solvent is selected from the group consisting of toluene, dimethylformamide, N-methyl-2-pyrrolidinone, and xylenes.

7. The process of claim 6, wherein the toluene is substantially removed from the mixture via step (b).

8. The process of claim 1, wherein the temperature of step (b) is in the range of about 126° C. to about 132° C.

9. The process of claim 1, wherein the mixture further comprises a suitable base.

10. The process of claim 9, wherein the suitable base is selected from the group consisting of pyridine, N,N-diisopropylethylamine (DIPEA), diazabicycloundecene (DBU), trimethylamine, and potassium benzoate.

11. The process of claim 1, wherein Form I has an x-ray powder diffraction pattern further comprising peaks at about the following 2θ values: 6.16, 10.95, 11.91, 14.60, 17.04, 17.23, 17.80, 19.18, 20.66, 21.10, 22.15, 23.50, 26.07, and 28.39.

* * * * *